US005723014A

United States Patent [19]
Laurent et al.

[11] Patent Number: 5,723,014
[45] Date of Patent: Mar. 3, 1998

[54] ORTHOPAEDIC IMPLANT HAVING A METALLIC BEARING SURFACE

[75] Inventors: Michel P. Laurent, Warsaw; Jerry Parcell, North Webster; Kent McDonald, Claypool, all of Ind.

[73] Assignee: Bristol-Myers Squibb Company, New York, N.Y.

[21] Appl. No.: 788,093

[22] Filed: Jan. 23, 1997

[51] Int. Cl.$^6$ ..................................................... A61F 2/30
[52] U.S. Cl. .......................................... 623/18; 623/22
[58] Field of Search .............................. 623/16, 18, 22, 623/23; 607/50, 51

[56] References Cited

U.S. PATENT DOCUMENTS

| | | |
|---|---|---|
| 3,892,648 | 7/1975 | Phillips et al. ........................ 204/181 |
| 3,964,473 | 6/1976 | Wickham et al. ...................... 623/23 |
| 4,195,367 | 4/1980 | Kraus ................................. 623/22 X |
| 4,214,322 | 7/1980 | Kraus ................................. 623/22 X |
| 4,216,548 | 8/1980 | Kraus ................................. 623/22 X |
| 4,506,673 | 3/1985 | Bonrell ................................. 607/50 |
| 5,205,921 | 4/1993 | Shirkanzadeh ....................... 205/318 |
| 5,211,833 | 5/1993 | Shirkanzadeh ....................... 205/322 |

Primary Examiner—Mary Beth Jones
Attorney, Agent, or Firm—Todd A. Dawson

[57] ABSTRACT

The invention is directed to an orthopaedic implant (30, 50) including a metallic body (42, 52) having a metallic bearing surface (44, 54). The orthopaedic implant also includes a device (46, 56) for applying an electromotive force to the metallic bearing surface (44, 54). The electromotive force may result from a galvanic couple with the bearing surface (44, 54) or a direct current power source (56) connected with the bearing surface (44, 54).

15 Claims, 2 Drawing Sheets

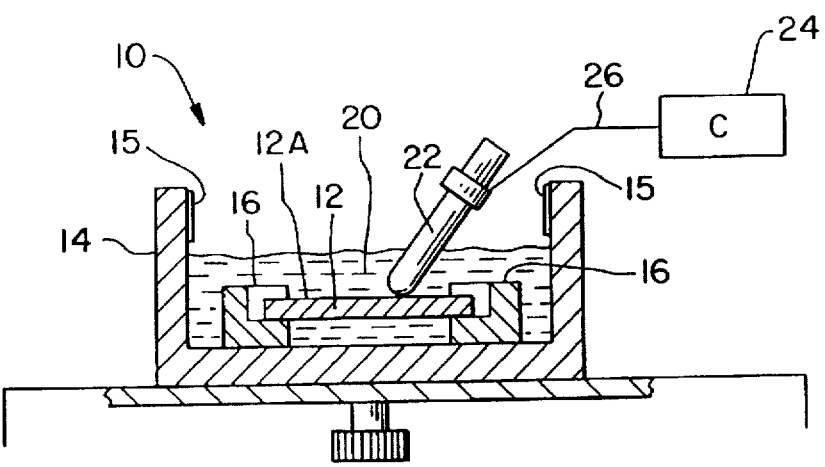
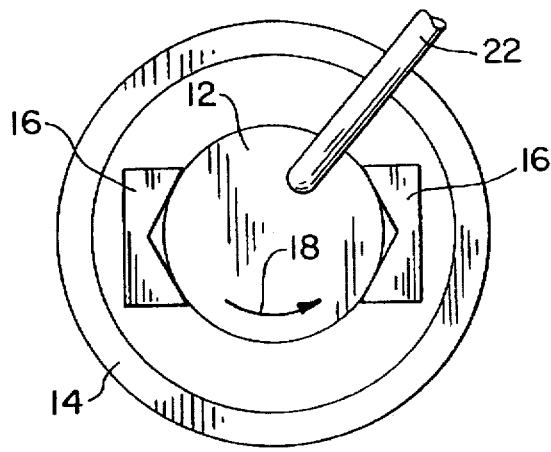
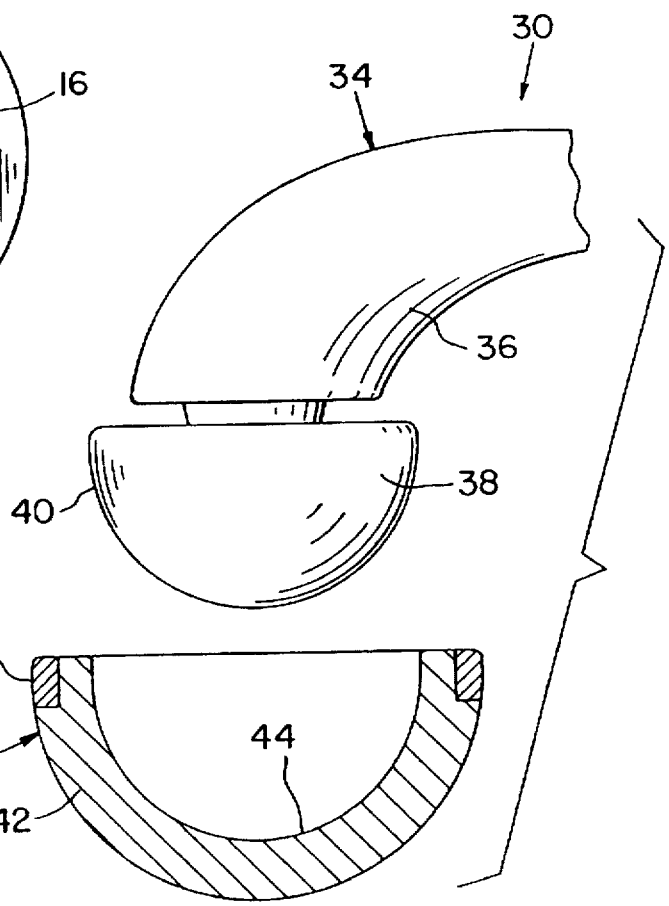

ORTHOPAEDIC IMPLANT HAVING A METALLIC BEARING SURFACE

BACKGROUND OF THE INVENTION

1. Field of the Invention

The present invention relates to orthopaedic implants, and, more particularly, to an orthopaedic implant having a metallic bearing surface.

2. Description of the Related Art

An orthopaedic implant which is used to replace a joint in a patient typically includes a bearing surface which engages and coacts with a bearing surface on an opposing implant. For example, in an orthopaedic hip replacement surgery, a bearing surface in the form of a head on a femoral implant is movably disposed against a bearing surface on an acetabular cup which is attached to the pelvic bone.

In an effort to reduce friction and improve wear characteristics between opposing bearing surfaces, one of the opposing bearing surfaces may be in the form of a non-metallic bearing surface such as ultra-high molecular weight polyethylene (UHMWPE). With reference again to an orthopaedic hip replacement surgery, the acetabular cup may include an UHMWPE liner which forms the associated bearing surface, and the femoral implant bearing surface may be formed from a cobalt-chromium-molybdenum alloy, titanium or stainless steel. The use of a metallic bearing surface on one orthopaedic implant and a polymeric bearing surface on an opposing orthopaedic implant has been found to be satisfactory in practice.

It is also known to use a pair of orthopaedic implants at a joint in a body which have opposing and coacting metallic bearing surfaces. For example, it may be possible to use a femoral implant having a bearing surface formed from a cobalt-chromium-molybdenum alloy which matingly engages with an acetabular cup having a bearing surface formed from a cobalt-chromium-molybdenum alloy. After such implants are implanted into the patient, the frictional force which occurs between the implants is a function of the coefficient of friction of the metallic materials, the normal contact force which exists between the bearing surfaces, and the effect of bodily fluids between the bearing surfaces as a lubricant.

What is needed in the art is an orthopaedic implant assembly which may be used at a joint in a patient, and which includes opposing and coacting metallic bearing surfaces with improved wear characteristics.

SUMMARY OF THE INVENTION

The present invention provides an orthopaedic implant having a metallic bearing surface with an electromotive force applied thereto, which results in improved wear characteristics of the bearing surface.

The invention comprises, in one form thereof, an orthopaedic implant including a metallic body having a metallic bearing surface. The orthopaedic implant also includes a device for applying an electromotive force to the metallic bearing surface. The electromotive force may result from a galvanic couple with the bearing surface or a direct current power source electrically coupled to the bearing surface.

An advantage of the present invention is that an orthopaedic implant having a metallic bearing surface with improved wear characteristics is provided.

Another advantage is that the overall exterior shape of the implant may remain relatively unchanged.

Yet another advantage is that the electromotive force which is applied to the metallic bearing surface may be generated using a battery, or one cathodic material and one anodic material.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is an example of a test fixture which is used to test materials for a bearing surface used in an orthopaedic implant;

FIG. 2 is a top view of the test fixture shown in FIG. 1;

FIG. 3 is an exploded, fragmentary, side view of an embodiment of an orthopaedic implant assembly of the present invention, using a galvanic couple in an acetabular cup.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 4:
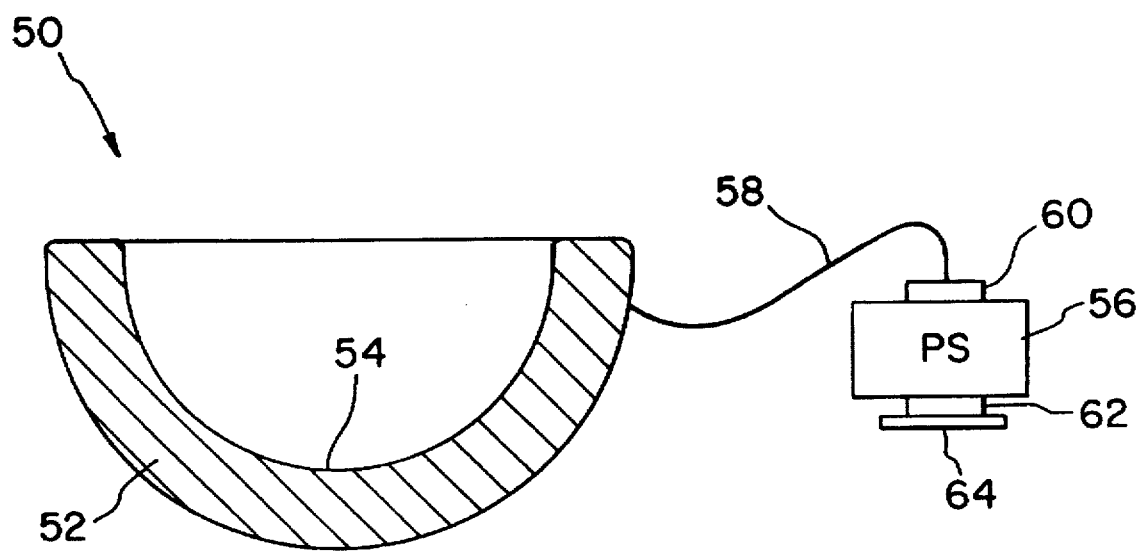
FIG. 4 is a side view of another embodiment of an orthopaedic implant of the present invention, using a battery connected with an acetabular cup.

Referring now to the drawings, and more particularly to FIGS. 1 and 2, there is shown an embodiment of a test fixture 10 which may be used to test materials for use as a bearing surface in an orthopaedic implant. A metallic body 12 in the form of a metallic disc is placed within test fixture 10 and tested to determine the wear characteristics thereof. Metallic body 12 is formed from a cathodic material such as a cobalt-chromium-molybdenum alloy. Body 12 is disposed within a container 14 and carried by a part holder 16.

Container 14 normally includes a layer of electrically insulative material 15 at the entire inside surface thereof. However, it has been found necessary with the present invention to remove at least a portion of the insulative material from the inside of container 14, and thereby electrically couple body 12 to container 14. In the embodiment of test fixture 10 shown in FIG. 1, the majority of the insulative material 15 has been removed from the inside surface of container 14. Alternatively, all of the insulative material 15 may be removed from the inside surface of container 14.

Part holder 16 carries body 12, as indicated above, and rotates body 12 at a selected rotational speed as indicated by arrow 18 in FIG. 2. Part holder 16 is preferably constructed from an electrically conductive material such as stainless steel. Container 14 contains body 12 and part holder 16 therein. Container 14 is constructed from an anodic material such as aluminum. Container 14 also includes an electrolytic fluid 20 therein which electrically interconnects body 12 with container 14. Electrolytic fluid 20 is preferably in the form of a mammalian bodily fluid such as bovine serum.

A test pin 22 exerts a predetermined axial load on body 12. Pin 22 is disposed at a predetermined inclination relative to a bearing surface 12A of body 12. In the particular embodiment shown in FIGS. 1 and 2, pin 22 is disposed at an inclination of approximately 30° relative to bearing surface 12A. Pin 22 is electrically connected to a controller (C) 24 via a line 26.

In operation, body 12 is submersed within bovine serum 20 contained within container 14. Body 12 and container 14 define a galvanic couple which defines an electromotive force in the form of an electrical potential between body 12 and container 14. More particularly, an electromotive force is applied to bearing surface 12A which results in improved wear characteristics of bearing surface 12A relative to wear characteristics of bearing surface 12A in an absence of such an electromotive force.

The above operation of test fixture 10 has also been conducted using a container 14 with an inside surface entirely covered by insulative material 15. Configured as such, container 14 is not electrically coupled to body 12 and the improved wear characteristics described above have not been observed.

Referring now to FIG. 3, an embodiment of an orthopaedic implant assembly 30 is shown. Orthopaedic implant assembly 30 includes a first orthopaedic implant 32 and a second orthopaedic implant 34. Second orthopaedic implant 34 includes a metallic body 36 in the form of a femoral implant which includes a femoral head 38. Femoral head 38 defines a metallic bearing surface 40 which matingly engages with first orthopaedic implant 32.

First orthopaedic implant 32 includes a first metallic body 42 in the form of an acetabular cup which may be implanted into a pelvic bone of a patient. Body 42 includes a metallic bearing surface 44 having a shape which matingly engages with bearing surface 40 of femoral head 38. Body 42 is formed from a cathodic material such as cobalt-chromium-molybdenum, titanium, stainless steel, or alloys thereof.

A metallic portion in the form of an annular ring 46 is attached to and carried by body 42. Annular ring 46 is constructed from an anodic material relative to the cathodic material from which body 42 is constructed. An example of an anodic material from which annular ring 46 may be constructed is aluminum. Other examples of anodic materials from which annular ring 46 may be formed include magnesium, zinc, galvanized steels, and alloys thereof. Annular ring 46 and body 42 define a galvanic couple therebetween. When orthopaedic implant 32 is in contact with an electrolytic fluid, such as a bodily fluid upon implantation into a patient, ions are allowed to flow across the electrical potential created by the electromotive force between body 42 and annular ring 46. It has been found in laboratory tests that the electromotive force results in improved wear characteristics of bearing surface 44, relative to wear characteristics of bearing surface 44 in an absence of such an electromotive force.

Referring now to FIG. 4, there is shown another embodiment of an orthopaedic implant 50 of the present invention. Implant 50 includes a metallic body 52 having a metallic bearing surface 54. Body 52 is constructed from a cathodic material, such as a cobalt-chromium-molybdenum alloy. Body 52 is electrically connected with an electric power supply (PS) 56 via a conductor 58. Power supply 58 is preferably in the form of a direct current battery having a first terminal 60 and a second terminal 62. First terminal 60 is directly connected to conductor 58 as shown. Second terminal 62 is connected to a thin disc or foil 64 which is formed from an electrically conductive and biologically inert material such as platinum or gold. Each of discs 64 and body 52 are disposed in communication with an electrolytic fluid, such that the electrolytic fluid completes the circuit between power supply 56 and body 52.

Power supply 56 is sized to provide an output which is necessary to establish an electrical potential sufficient to improve the wear characteristics of bearing surface 54. Each of body 52 and power supply 56 are implanted within a patient and disposed in fluid communication with the bodily fluid which acts as an electrolyte. The electrical potential of the battery causes an electromotive force which improves the wear characteristics of bearing surface 54.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant, comprising:
    a metallic body including a metallic bearing surface; and
    means for applying an electromotive force to said metallic bearing surface.

2. The orthopaedic implant of claim 1, wherein said means for applying said electromotive force comprises a metallic portion attached to said body, said body comprised of a cathodic material and said metallic portion comprised of an anodic material relative to said body, whereby an electrical potential is created between said body and said metallic portion.

3. The orthopaedic implant of claim 2, wherein said body and said metallic portion define a galvanic couple.

4. The orthopaedic implant of claim 2, wherein said body is comprised of a cobalt-chromium-molybdenum alloy and said metallic portion is comprised of aluminum.

5. The orthopaedic implant of claim 2, wherein said body defines an acetabular cup and said metallic portion comprises an annular ring carried by said body.

6. The orthopaedic implant of claim 1, wherein said means for applying said electromotive force comprises an electric power supply which is electrically connect with said body.

7. The orthopaedic implant of claim 6, wherein said power supply comprises a direct current battery.

8. The orthopaedic implant of claim 1, wherein said means for applying said electromotive force results in improved wear characteristics of said bearing surface, relative to wear characteristics of said bearing surface in an absence of said applying means.

9. An orthopaedic implant assembly, comprising:
    a first orthopaedic implant including a first metallic body having a first metallic bearing surface, said first implant further including means for applying an electromotive force to said first bearing surface; and
    a second orthopaedic implant including a second metallic body having a second metallic bearing surface, said second bearing surface configured to matingly engage with said first bearing surface.

10. The orthopaedic implant assembly of claim 9, wherein said means for applying said electromotive force comprises a metallic portion attached to said first body, said first body comprised of a cathodic material and said metallic portion comprised of an anodic material relative to said first body, whereby an electrical potential is created between said first body and said metallic portion.

11. The orthopaedic implant assembly of claim 10, wherein said first body and said metallic portion define a galvanic couple.

12. The orthopaedic implant assembly of claim 10, wherein said first body is comprised of a cobalt-chromium-molybdenum alloy and said metallic portion is comprised of aluminum.

13. The orthopaedic implant assembly of claim 10, wherein said first body defines an acetabular cup and said metallic portion comprises an annular ring carried by said body.

14. The orthopaedic implant assembly of claim 9, wherein said means for applying said electromotive force comprises an electric power supply which is electrically connected with said first body.

15. The orthopaedic implant assembly of claim 9, wherein said power supply comprises a direct current battery.

* * * * *